(12) United States Patent
Sone

(10) Patent No.: US 6,529,848 B2
(45) Date of Patent: Mar. 4, 2003

(54) THERMAL ANALYSIS APPARATUS

(75) Inventor: Yuuya Sone, Chiba (JP)

(73) Assignee: Seiko Instruments Inc. (JP)

(*) Notice: Subject to any disclaimer, the term of this patent is extended or adjusted under 35 U.S.C. 154(b) by 75 days.

(21) Appl. No.: 09/734,268

(22) Filed: Dec. 11, 2000

(65) Prior Publication Data

US 2001/0004730 A1 Jun. 21, 2001

(30) Foreign Application Priority Data

Dec. 20, 1999 (JP) .......................................... 11-361703

(51) Int. Cl.$^7$ .......................... G01N 25/00; G06F 15/46
(52) U.S. Cl. .......................... 702/130; 702/132; 379/39; 340/540
(58) Field of Search .............................. 379/39, 41, 42; 340/539, 511, 506; 702/130, 132; 700/286; 709/208

(56) References Cited

U.S. PATENT DOCUMENTS 5,568,535 A 10/1996 Sheffer et al. ................ 379/39
5,729,197 A 3/1998 Cash .......................... 340/539

FOREIGN PATENT DOCUMENTS

EP 0920210 6/1999
EP 0959347 11/1999

Primary Examiner—Kamini Shah
(74) Attorney, Agent, or Firm—Adams & Wilks

(57) ABSTRACT

The problem the present invention sets out to resolve is to detect events regardless of the condition of the system operation, and notify one or a plurality of users at remote locations of the detected events using a message. To solve the above problem, apparatus relating to the present invention comprise a measurement module with a heating furnace installed, a measurement station with a measurement user interface for controlling the measurement module, a personal computer or a workstation connected to the measurement station via communication media, a pager connected to the measurement station via a public telephone line, and a software operating on a central processing units installed in the measurement module, the measurement station, and the personal computer or the workstation.

14 Claims, 5 Drawing Sheets

THERMAL ANALYSIS APPARATUS

BACKGROUND OF THE INVENTION

The present invention relates to apparatus for thermal analysis.

Thermal analysis is a way of measuring physical changes of samples while changing the temperature, for temperatures in a range of from below-freezing temperature to 1500° C. Temperatures are measured by scanning a temperature range to be measured by raising temperature at an appropriate rate (in units of ° C./min). The length of time a measurement is made for is decided according to the rate of rising and the temperature range. The measuring time is usually somewhere around ten minutes to an hour, although a couple of hours to several days may be required for long measurements. As it is not necessary to operate the apparatus during measurements, in most cases, users merely keep on monitoring the apparatus while measurements are being taken. Therefore, cases where users carry out other work at a different location remote from the laboratory where the apparatus is installed are common.

In the situation described above, when some kind of trouble occurs that causes the measurements to be suspended, users are required to solve the problem and perform the measurements again.

However, as users are often located in a place far from the apparatus, they sometimes may not be aware that a problem has occurred. As the user may therefore neglect the apparatus without noticing that measurements have been interrupted, this may mean that an unnecessarily large amount of time may pass before measurements are restarted. The occurrence of problems rendering the apparatus uncontrollable also causes time to be wasted while carrying out measurements. Moreover, when a sample to be measured exhibits a fusion reaction, cases where proceeding with measurements beyond a certain preset value may ruin the sensor as the melted sample adheres onto it are common.

To enable more effective measurement, in the case of the occurrence of certain events such as, for example, the arrival of a signal notifying that a certain preset value is reached, the completion of a measurement, or an event where trouble has occurred within the apparatus, etc., it is preferable for the user to be notified of this situation in real time, wherever the apparatus may be.

Related technology for monitoring apparatus located at a remote location exist, such as, (1) monitoring measuring conditions via a network (Japanese Patent Laid-open Publication No. Hei. 9-325024), (2) suspend the operation of apparatus upon the occurrence of errors posing risks (Japanese Patent Laid-open Publication No. Hei. 5-19880), (3) manage the apparatus by utilizing E-mail (Japanese Patent Laid-open Publication No. Hen. 9-32950), However, the following problems exist with this related technology.

The means for monitoring the measuring conditions via a network as disclosed in (1) above requires a user to keep observing the conditions at the place the monitor is installed while operating the monitor periodically. However, this means is not effective when a user is not on location, or forgets to observe the conditions.

The means for suspending the operation of apparatus upon the occurrence of an error posing risk as disclosed in (2) above can avoid risk for the time being, but the user will not be notified of the suspension at real time.

When the system itself halts as the result of the trouble occurring at the system control unit, neither (1) nor (2) disclosed above can detect the trouble.

With (1) or (2), the apparatus is monitored only by the user executing the measurements, and a number of people therefore cannot be aware of the emergency.

The means to monitor the apparatus using e-mail as disclosed in (3) above includes a similar problem to (1) above. Moreover, a time lag exists in order to retrieve e-mail from a mail server and users therefore cannot be notified in real time.

In order to resolve the aforementioned problems, the present invention sets out to provide an apparatus for thermal analysis with a monitoring unit installed separately from the system control unit so that an event occurring within the apparatus can be detected regardless of system operation conditions in real time and regardless of the location of the users, and the detected content can be notified to one or a plurality of users by transmitting a message.

SUMMARY OF THE INVENTION

The present invention was developed to resolve the aforementioned problems, and the main element of the configuration comprises a heating furnace, a temperature sensor, a physical quantity sensor, control measurement means, system control means, a storage device, an input output (I/O) unit, event monitoring means, event control means, information setting transmission means, message transmission means, message receiving means, user interface means, and a communication medium.

DETAILED DESCRIPTION OF THE PREFERRED EMBODIMENT

The following description is now given of an embodiment of the present invention based on the appended drawings.

Figure 1:
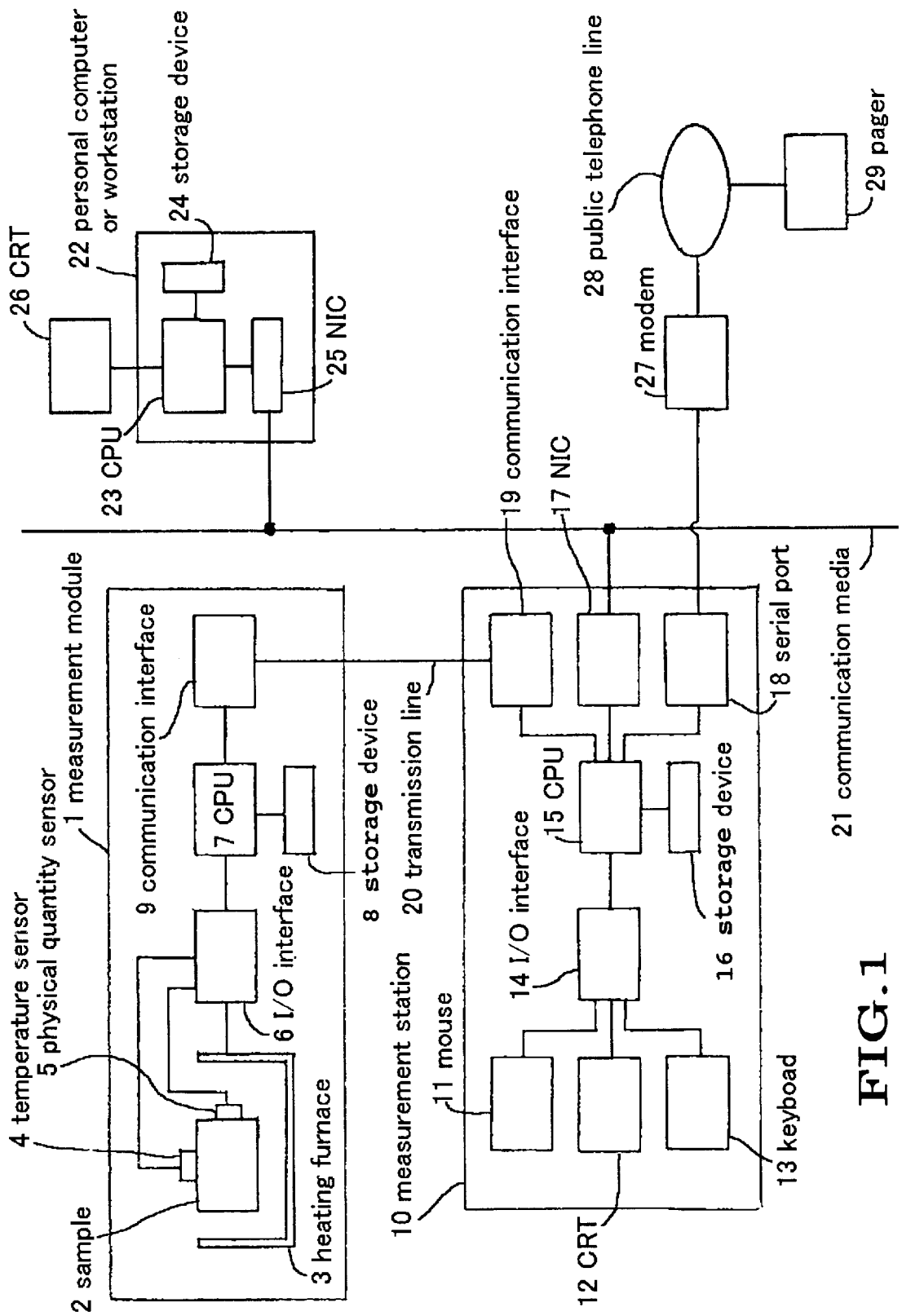
FIG. 1 is a drawing showing a hardware configuration of an embodiment of the present invention

FIG. 1 is a view showing a hardware configuration of the embodiment of the present invention.

The measurement module 1 detects the heating, temperature and physical quantity of the sample 2 according to a designation from the measurement station 10, and transmits the data to the measurement station 10. The measurement module 1 functions with the measurement control software processed at the central processing unit 7 and the storage device 8 installed in the measurement module 1 (the measurement control software operates as a task at the central processing unit 7 and the storage device 8 installed in the measurement module 1 and is hereinafter referred to as a measurement control task).

The measurement station 10 controls a plurality of measurement modules 1, receives data from the measurement module 1, and executes thermal analysis. The measurement station 10 functions with the measurement control software processed at the central processing unit 15 and the storage device 16 installed in the measurement station 10 (the system control software activates as a task at the central processing unit 15 and the storage device 16 installed in the measurement station 10, hereinafter referred to as a system control task).

Users of the apparatus for the thermal analysis place the sample 2 into the heating furnace 3 of the measurement module 1. The change of temperature of the sample 2 is then detected with the temperature sensor 4, and the change of physical quantity of the sample 2 is detected with the physical quantity sensor 5. The temperature sensor 4 evaluates the temperature of or in the vicinity of sample 2. The physical quantity sensor 5 detects, for example, the heat flow to the sample 2 with DSC, the change of the weight of the sample 2 with TG, or the change of shape of the sample 2 with TMA. The heating furnace 3, the temperature sensor 4, and the physical quantity sensor 5 are connected to the 10 interface 6 installed in the measurement module 1, and the central processing unit 7 is installed in the measurement module 1. Temperature control of the heating furnace 3 is executed by the central processing unit 7 installed in the measurement module 1, which is connected to the heating furnace 3 via the I/O interface 6 installed in the measurement module 1. The central processing unit 7 installed in the measurement module 1 is connected to the measurement station 10 via the communication interface 9 installed in the measurement module unit 1.

The measurement station 10 monitors user interfaces relating to measurements, control designations to a plurality of measuring modules, and events for data accumulation and measurement control tasks and system control tasks using a so-called personal computer or workstation. The measurement station 10 performs the functions of a general operating system, such as Windows, Windows-NT, UNIX, etc., system control software and event monitoring software. The event monitoring software has the functions of event monitoring, message control, and setting transmission information.(The function of the event monitoring software operates as a task at the central processing unit 15 and the storage device 16 installed in the measurement station 10. This is referred to hereinafter as an event monitoring task, message control task, and transmission information setting task).

The central processing unit 15 installed in the measurement station 10 is connected to the plurality of measurement module units 1 via the communication interface 19 and the transmission line 20 installed in measurement station 10 . Any general communication line such as RS-232C, GP-IB, or SCSI can be adopted as the transmission line 20.

Figure 2:
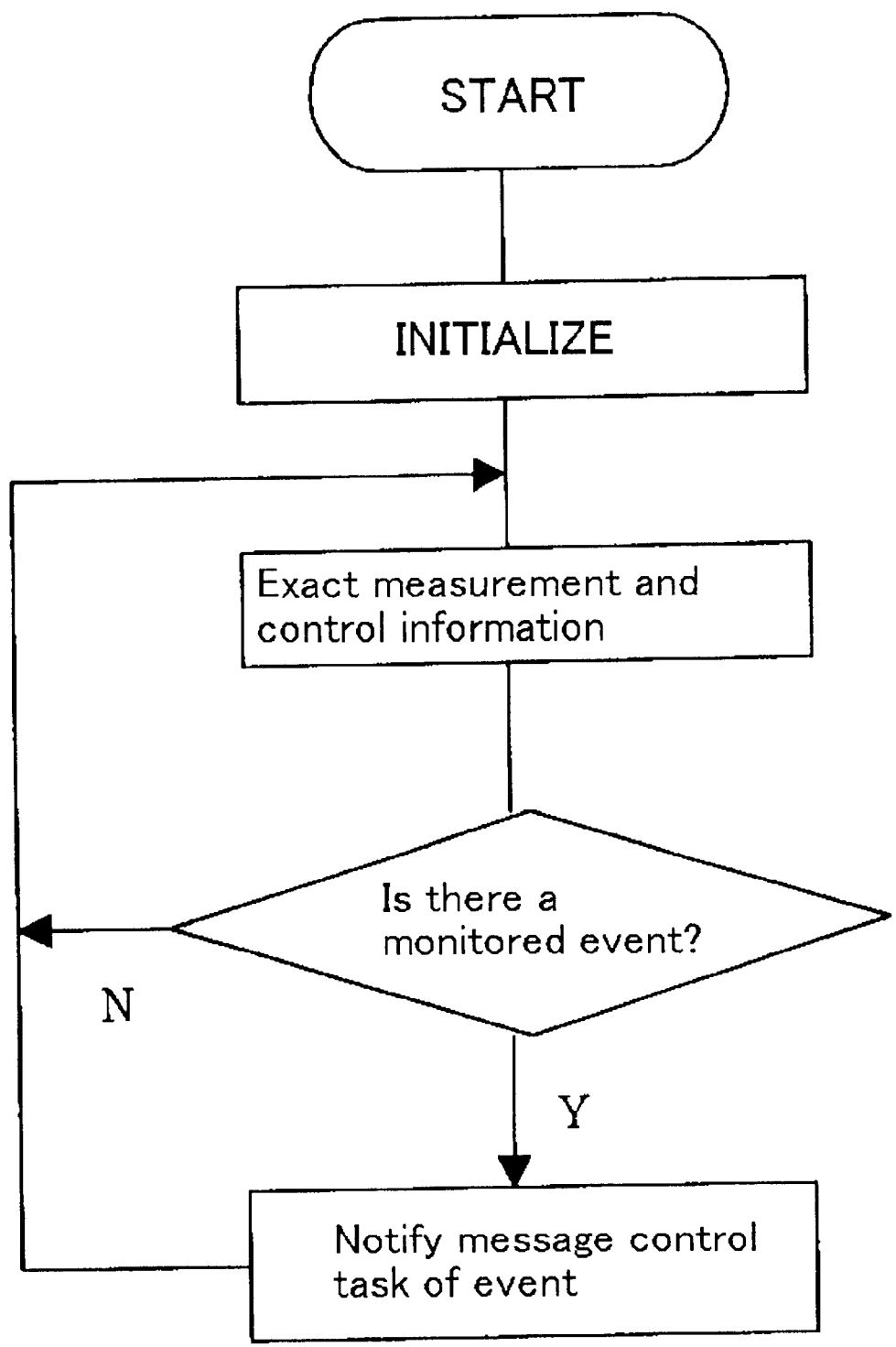
FIG. 2 is an algorithm of a task for event monitoring of an embodiment of the present invention

Control information related to the operation, error information of the software/hardware, and measured signals, etc. are exchanged between the measurement control task and the system control task via the transmission line 20. The event monitoring task monitors the information being exchanged via the transmission line 20 periodically with the timer according to the algorithm described in FIG. 2, and detects arbitrary information preselected by the user as events, such as a signal notifying that measurement has reached a certain preset value, the completion of the measurement, the occurrence of an error, or the suspension of a task, etc. The measurement control task and the system control task activate independently from each other, so that monitoring can be executed regardless of the influence of a failure occurring for either one of the tasks. When an event is detected, the event will be transmitted to the message control task (Any means such as DDE, IPC, and COM, etc. can be adopted as the means for communication between tasks).

Figure 3:
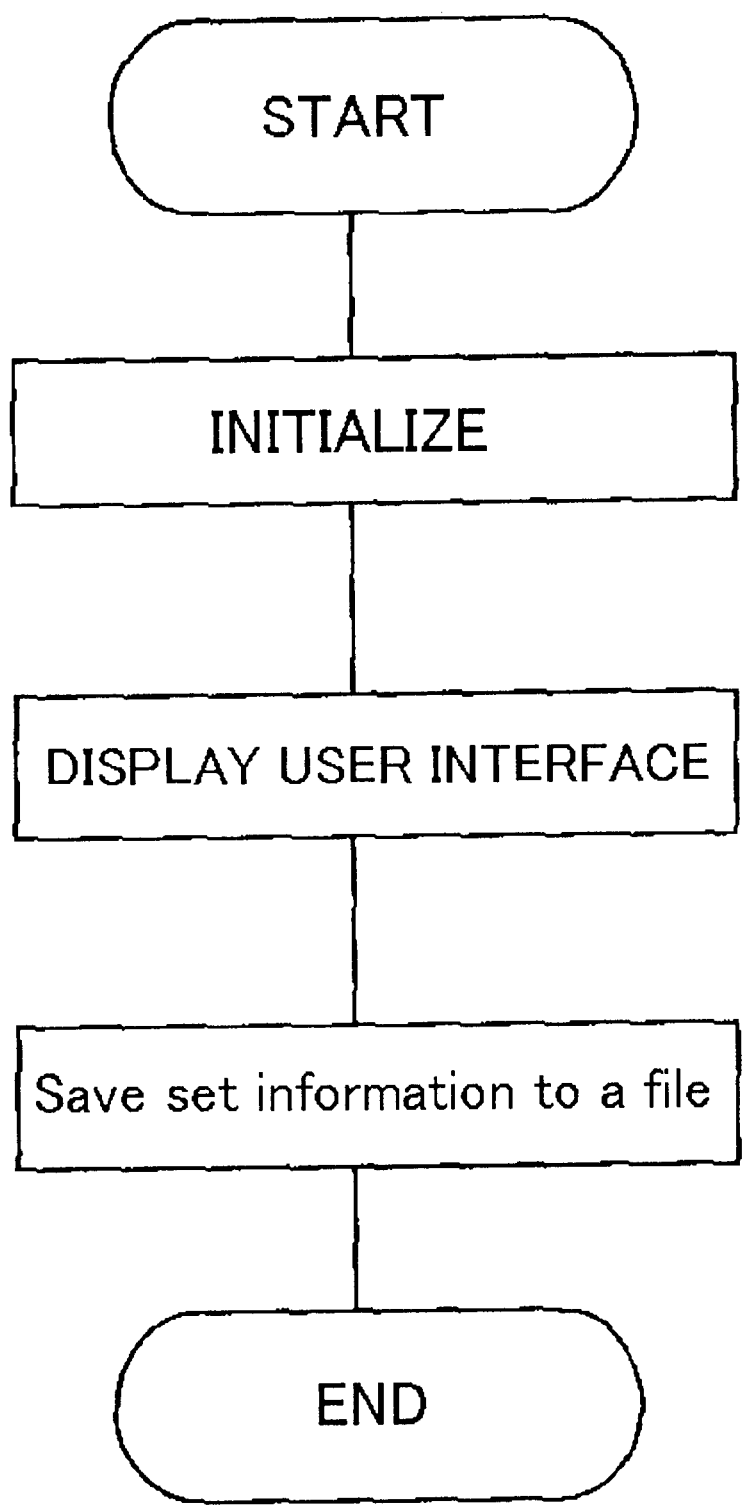
FIG. 3 is an algorithm for a transmission information setting task of an embodiment of the present invention.

The transmission information setting task has functions to set the destination to transmit the message to and the event to monitor. A GUI is provided, and a user can arbitrarily select the destination to transmit the message to and an event to monitor with the mouse 11, CRT 12, and keyboard 13 installed in the monitoring station 10 (an algorithm for a transmission information setting task is shown in FIG. 3).

The personal computer or the workstation 22 connected to the communication media 21, or a pager 29 connected via the public telephone line 28 can be selected as a message destination.

When transmitting a message to the personal computer or the workstation 22 connected to the communication media 21 such as the local area network, the user can select whether to transmit only to a specific computer or to broadcast to every computer connected to the network. The IP address of the destination computer is designated when transmitting to a specific computer and an IP address decided in advance for broadcast communication is designated for broadcast communication.

When a message is transmitted to the pager 29 via the pubic telephone line 28, the telephone number of the pager 29 is designated. When a message is transmitted to the pager 29, the message can be transmitted to a plurality of telephone numbers at the same time.

The options of the event to monitor are;

1 step of the temperature program completed.

Measurement completed.

A software error occurred at a measurement module.

A hardware error occurred at a measurement module.

A measurement control task has been suspended.

A software error occurred at a measurement station.

A system control task has been suspended. etc. related to the completion of the process and trouble report. In addition to those, The signal has reached the preset value.

The temperature of the heating furnace has reached the preset value.

and signals during measurements and the condition of the temperature of the heating furnace are available as events. Those options are provided to meet the frequent needs in the thermal analysis to understand the condition of a measurement at any time demanded.

The message transmission information as set above is stored in the storage device 16 installed in the measurement station 10.

Figure 4:
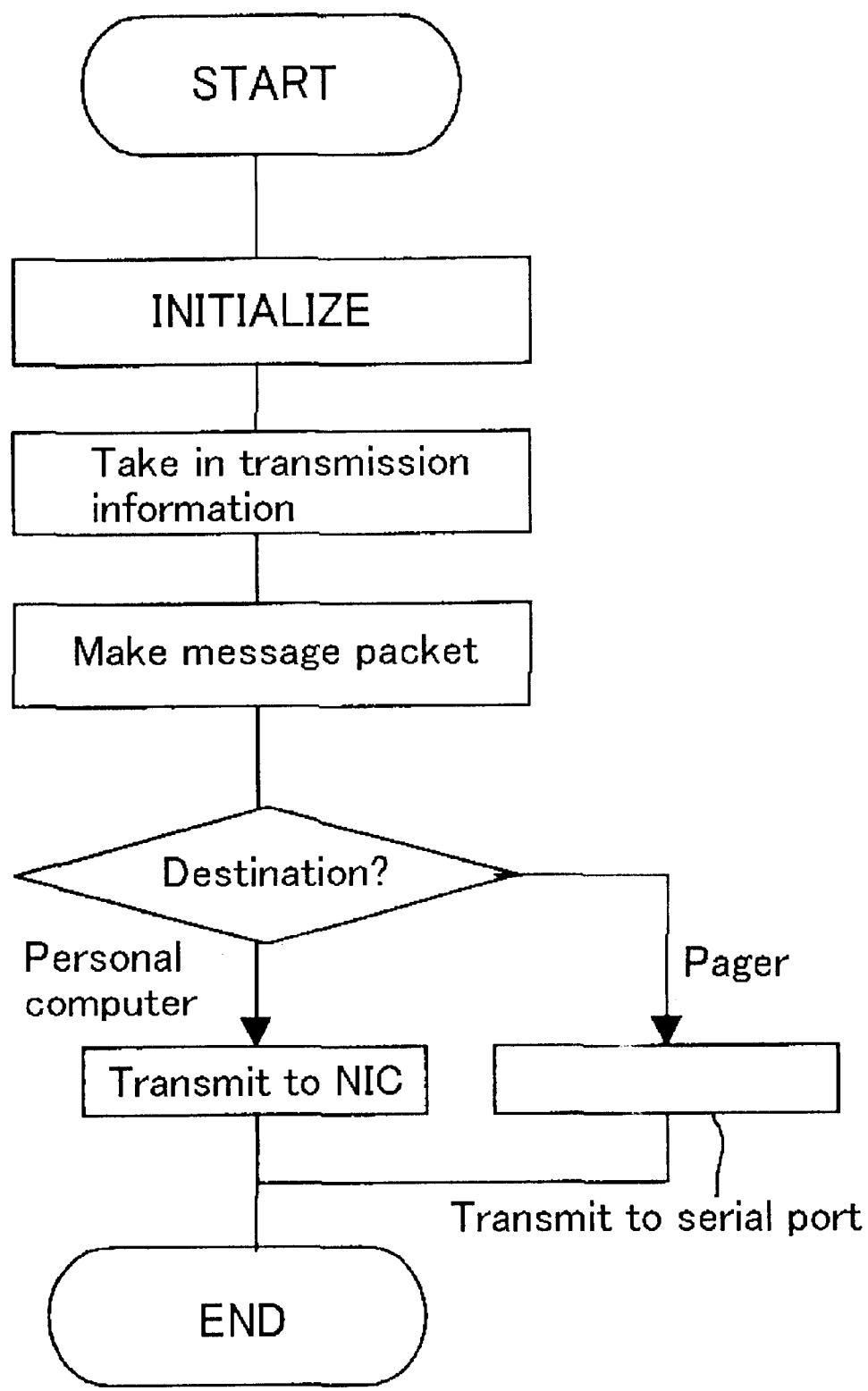
FIG. 4 is an algorithm of a message control task of an embodiment of the present invention.

The message control task creates a message packet consisting of the message and the destination to transmit the message to, that correspond to the event transmitted from the event monitoring task according to the message transmission information stored in the storage device 16 installed in the measurement station 10, according to TCP/IP protocol (FIG. 4 shows the algorithm of the message control task).

To transmit a message to the personal computer or workstation 22 connected to the communication media 21 such as local area network, the created message packet will be transmitted to the communication media 21 via the network interface card (hereafter referred to as NIC) 25.Any dedicated network such as Ethernet, FDDI, or Token Ring can be adopted as the communication media 21.

When transmitting a message to the pager 29, the message is transmitted to the serial port 18 to which the modem 27 is connected. The modem 27 is connected to the public telephone line 28, and transmits the message packet to the pager 29 via the public telephone line 28. The technology for transmitting a message to the pager 29 via the public telephone line 28 and displaying the message is a well known technology.

Figure 5:
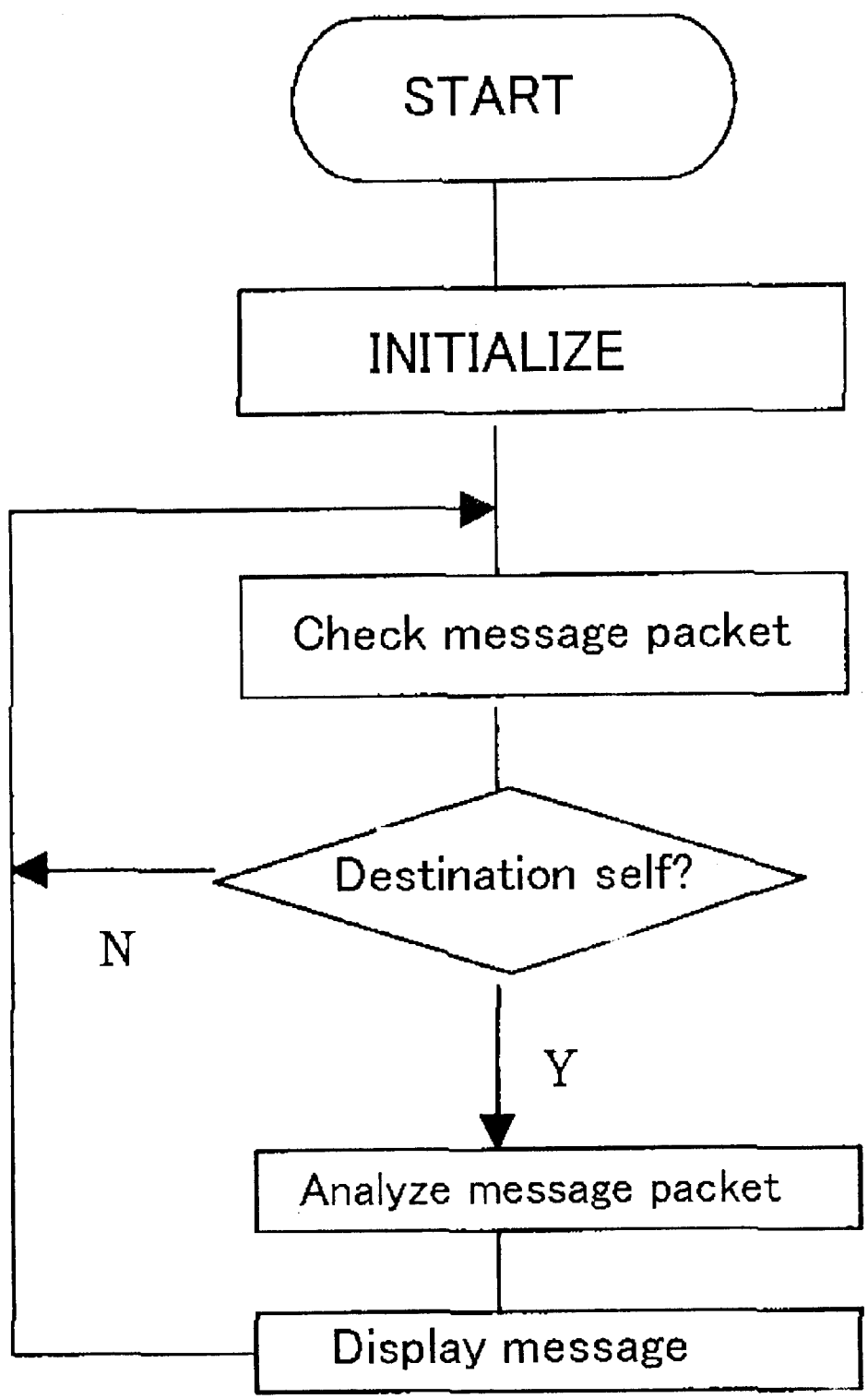
FIG. 5 is an algorithm for message receiving of an embodiment of the present invention.

The so-called personal computer or workstation 22 is employed as the means for receiving message packets flowing in the communication media 21 such as local area network. The personal computer functions as a general operating system, such as Windows, Windows-NT, UNIX, etc., and as message receiving software (the message receiving software which operates on the personal computer or the workstation 22 will be referred as the message receiving task hereafter). The message receiving task has a function for receiving message packets flowing among the communication media 21 and the function of GUI to display the message on CRT 25. The message receiving task always resides in the memory installed in the personal computer or the workstation 22, and monitors the message packets flowing in the communication media 21 via the NIC 25 installed on the personal computer or the workstation 22 according to the algorithm shown in FIG. 5. When the destination of the transmitted message is itself, it receives the message packet and notifies users of events that have occurred within the apparatus by retrieving the message from the message packet for displaying on the CRT 26 utilizing the GUI.

As described above, in the present invention, events are monitored independently from the system control, and messages are transmitted to a computer or a pager at a remote location via the communication media, so that users are notified of the condition of the apparatus without paying special attention to it, in real time at any location;

so that users can operate the apparatus more effectively and more safely.

What is claimed is:

1. An apparatus for thermal analysis comprising:

heating means for heating a sample;

a temperature sensor for detecting the temperature of, or in the vicinity of, the sample and outputting a corresponding signal;

a physical quantity sensor for detecting a changing physical quantity of the sample in accordance with changes in temperature;

one or more measurement control means for controlling the heating means and transmitting signals detected by the temperature sensor and the physical quantity sensor to a system side via a transmission line;

system control means connected by the transmission line to the one or more measurement control means for controlling the measurement control means, receiving signals detected by the measurement control means, and executing thermal analysis;

a storage device for storing signals detected by the measurement control means and commands for processing by the system control means;

an input/output unit for outputting results of thermal analysis obtained by the system control means from commands input by a user;

event monitoring means operating independently of the measurement control means and the system control means for periodically monitoring events occurring at the measurement control means and the system control means;

message control means for receiving a signal notifying of the occurrence of an event from the event monitoring means, assembling a message packet including a message and a destination to which the message is to be transmitted to according to the event, and executing a command to transmit the message packet;

transmission information setting means for setting information relating to message transmissions utilized by the message control means;

message transmission means for receiving a message packet from the message control means, and transmitting the message packet to a communication media;

message receiving means for retrieving message packets flowing in the communication media; and user interface means for displaying a message included in the retrieved message packet.

2. An apparatus for thermal analysis according to claim 1; wherein the transmission information setting means has means for permitting user selection of events to be monitored and destinations to which messages are to be transmitted.

3. An apparatus for thermal analysis according to claim 1; wherein the message transmission means includes means for transmitting a message to one or a plurality of the message receiving means connected to the communication media.

4. An apparatus for thermal analysis according to claim 1; wherein the message transmission means includes means for broadcasting a message to every message receiving means connected to the communication media at the same time.

5. An apparatus for thermal analysis according to claim 1; wherein the message control means includes means for creating messages receivable by a pager, and for transmitting messages to a pager via a public telephone line.

6. An apparatus for thermal analysis according to claim 1; wherein the event monitoring means operate independently from the system control means and the measurement control means so that suspension of the functions of the system control means and the measurement control means can be detected in real time.

7. An apparatus comprising;

a heating furnace for heating a sample;

a temperature sensor for detecting the temperature of, or in the vicinity of, the sample;

a physical quantity sensor for detecting a changing physical quantity of the sample in accordance with change in temperature;

one or more measurement control tasks for controlling the heating furnace and transmitting signals detected by the temperature sensor and the physical quantity sensor to a system side via a transmission line;

a system control task connected to more than one measurement control task by the transmission line for controlling the one or more measurement control tasks, receiving signals detected by the measurement control tasks, receiving signals detected by the measurement control tasks, and executing thermal analysis;

a storage device for storing signals detected by the measurement control tasks and commands for processing by the system control task;

an input/output unit for outputting results of thermal analysis obtained by the system control means from commands input by a user;

an event monitoring task independent of the measurement control tasks and the system control task for periodically monitoring events occurring within the measurement control task and the system control task;

a message control task for receiving a signal notifying of an occurrence of an event from the event monitoring task, assembling a message packet including a message and a destination to which the message is to be transmitted to in correspondence with the event, and executing a command to transmit the message packet;

a transmission information setting task for setting information related to message transmission utilized in the message control task;

message transmission means for receiving a message packet from the message control task, and transmitting the message packet to the communication media;

message receiving means for retrieving a message packet flowing at the communication media;

and user interface means for displaying a message included in the retrieved message packet.

8. A thermal analyzer comprising: a plurality of measurement units each for heating a sample to perform thermal analysis thereof; a system control unit for controlling the plurality of measurement units and being connected to the measurement units via a transmission line; an event monitoring unit operating independently of the measurement units and the system control unit for periodically monitoring for specified events occurring at the measurement units and the system control unit; and a message transmission unit for receiving notification of the occurrence of a specified event from the event monitoring unit and transmitting a message to a remote user over a communication medium.

9. A thermal analyzer according to claim 8; wherein the measurement units comprise a furnace for heating a sample, a temperature sensor for detecting the temperature of or in the vicinity of the sample and outputting a corresponding signal, a physical quantity sensor for detecting a changing physical quantity of the sample in accordance with changes in temperature, and measurement control means for controlling the furnace and transmitting signals detected by the temperature sensor and the physical quantity sensor to the system control unit via the transmission line.

10. A thermal analyzer according to claim 9; wherein the system control unit receives signals detected by the measurement control means and executes thermal analysis.

11. A thermal analyzer according to claim 10; further comprising a storage unit for storing signals detected by the measurement control unit and commands for processing by the system control unit.

12. A thermal analyzer according to claim 8; further comprising an input/output unit for outputting results of thermal analysis obtained by the system control unit based on commands input by a user and received over the communication medium.

13. A thermal analyzer according to claim 8; wherein the message transmission unit comprises message control means for receiving a signal notifying of the occurrence of a specified event from the event monitoring unit, assembling a message packet including a message and a destination to which the message is to be transmitted to according to the event, and executing a command to transmit the message packet; transmission information setting means for setting information relating to message transmissions utilized by the message control means; and message transmission means for receiving a message packet from the message control means, and transmitting the message packet to the user over the communication media.

14. A thermal analyzer according to claim 13; further comprising user interface means for displaying a message included in the retrieved message packet.

* * * * *